United States Patent
Rodríguez del Val

(10) Patent No.: US 7,090,492 B2
(45) Date of Patent: Aug. 15, 2006

(54) ELEMENT FOR AIDING IN THE CEMENTATION OF FIXED DENTAL PROSTHESIS

(76) Inventor: José María Rodríguez del Val, Avda. del Cid 3, 3° G, 09003 Burgos (ES)

( * ) Notice: Subject to any disclaimer, the term of this patent is extended or adjusted under 35 U.S.C. 154(b) by 251 days.

(21) Appl. No.: 10/246,353

(22) Filed: Sep. 18, 2002

(65) Prior Publication Data
US 2003/0054320 A1 Mar. 20, 2003

(51) Int. Cl.
*A61C 5/00* (2006.01)

(52) U.S. Cl. ...................................... 433/140; 433/136

(58) Field of Classification Search ................ 433/136, 433/140; 128/857, 861; 600/237, 238
See application file for complete search history.

(56) References Cited

U.S. PATENT DOCUMENTS

| | | | | |
|---|---|---|---|---|
| 2,023,288 A | * | 12/1935 | Pickett | 600/238 |
| 3,352,301 A | * | 11/1967 | Abelson | 600/237 |
| 3,523,535 A | * | 8/1970 | Verner et al. | 604/366 |
| 3,722,101 A | | 3/1973 | Via Jr. | |
| 3,903,606 A | * | 9/1975 | Oliver | 433/141 |
| 4,335,721 A | * | 6/1982 | Matthews | 604/363 |
| D267,586 S | * | 1/1983 | Hatlen | D24/176 |
| 4,541,803 A | | 9/1985 | Adler | 433/141 |
| 4,573,919 A | * | 3/1986 | Sinkora | 433/140 |
| 4,657,509 A | | 4/1987 | Morris | 433/37 |
| D297,665 S | * | 9/1988 | Neeley | D24/176 |
| 4,869,669 A | * | 9/1989 | Grubbs | 433/140 |
| 4,975,053 A | * | 12/1990 | Hofsess | 433/25 |
| 5,320,114 A | * | 6/1994 | Kittelsen et al. | 128/861 |
| 5,454,719 A | * | 10/1995 | Hamblen | 433/215 |
| 5,469,865 A | * | 11/1995 | Minneman | 128/859 |
| 5,927,972 A | * | 7/1999 | Humboldt | 433/25 |
| 6,200,046 B1 | * | 3/2001 | Rylander | 401/52 |
| 6,241,521 B1 | * | 6/2001 | Garrison | 433/140 |
| 6,634,884 B1 | * | 10/2003 | Phillips | 433/138 |

FOREIGN PATENT DOCUMENTS

| GB | 2 366 735 A | * | 3/2002 |
|---|---|---|---|
| JP | 245290 | * | 9/2003 |

* cited by examiner

*Primary Examiner*—Ralph A. Lewis
(74) *Attorney, Agent, or Firm*—Brown & Michaels, PC

(57) ABSTRACT

An element for aiding in the cementation of a fixed dental prosthesis that results in equal pressure being applied to the prosthesis comprising a block having a first end (M) and a second end (d). The first end (M) is thicker than the second end (d), and when the first end is mesially placed and the second end is distally placed between two dental arcades, equal pressure is applied to the prosthesis. The block may be frustropyramidal, frustroconical, or helical in shape.

4 Claims, 2 Drawing Sheets

ELEMENT FOR AIDING IN THE CEMENTATION OF FIXED DENTAL PROSTHESIS

BACKGROUND OF THE INVENTION

1. Field of the Invention

The invention pertains to the field of dentistry. More particularly, the invention pertains to cementation of fixed dental prosthesis.

2. Description of Related Art

Teeth are permanently lost in a variety of ways, the most common being dental decay, periodontal (gum) disease, accidental trauma, and injury. The teeth that are lost need to be replaced so that the neighboring teeth are not affected. The treatment for the permanent loss of one or more teeth is a bridge. A bridge spans the space or dental arch where one or more teeth have been lost. The treatment consists of preparation of the area, fitting of the bridge, and cementation of the bridge.

During the cementation step of permanently fixing the bridge, the dentist uses cylindrical shaped cotton blocks to help keep the bridge fixed in one place while it is being permanently cemented into place. The cylindrical shaped cotton balls are manufactured specifically for absorbing saliva, not for aiding in cementation.

When a patient bites down on the cylindrical shaped blocks, the bottom row (arcade) of teeth and the upper row (arcade) of teeth connect at a rear point, opening up in an angle that causes the pressure to be greater in the distal or rear part of the mouth then in the mesial or front part of the mouth. This imbalance of pressure causes the bridge that is being cemented into place to tilt.

Therefore, an aid was needed for the cementation of a prosthesis that does not causes an unequal distribution of pressure between the distal and mesial portions of the mouth.

SUMMARY OF THE INVENTION

An element for aiding in the cementation of a fixed dental prosthesis that results in equal pressure being applied to the prosthesis comprising a block having a first end (M) and a second end (d). The first end (M) is thicker than the second end (d), and when the first end is mesially placed and the second end is distally placed between two dental arcades, equal pressure is applied to the prosthesis. The block may be frustropyramidal, frustroconical, or helical in shape.

DETAILED DESCRIPTION OF THE INVENTION

Figure 1:
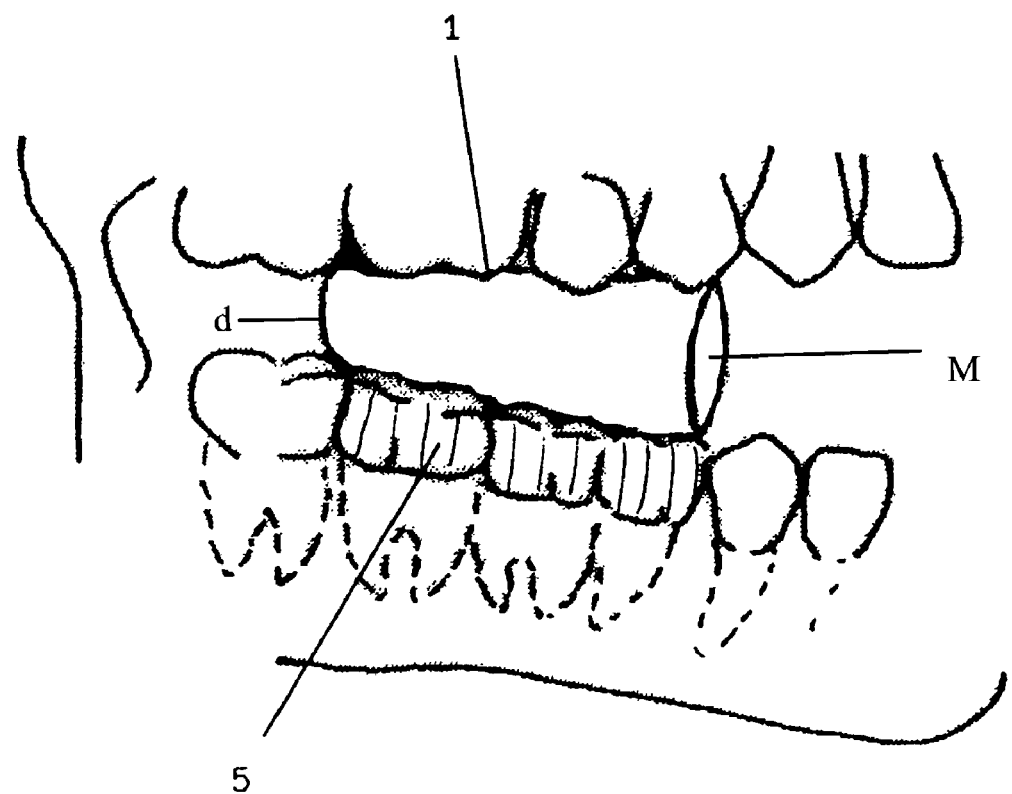
FIG. 1 shows the jaw of a patient when biting on the present invention to aid in the cementation of a fixed dental prosthesis.

FIG. 1 shows the element (1) being bitten on by a patient after placing a fixed dental prosthesis (5). The element (1) comprises a block elongated in wedge formation, which is thicker on one end (M) than on the other (d), thus being adapted to placement between the two dental arcades by arranging the thick end (M) in the mesial portion of the mouth and the thinner end (d) in the distal portion of the mouth. The element (1) aids in cementation by exerting equal pressure on the teeth in both the distal and mesial portions of the mouth.

Figure 2:
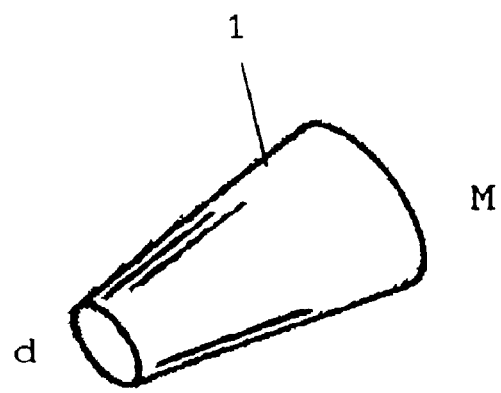
FIG. 2 shows an alternative embodiment of the present invention.
Figure 3:
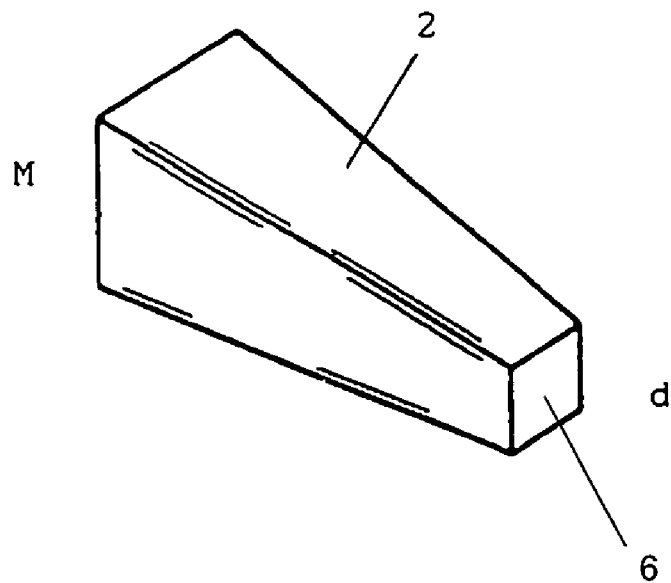
FIG. 3 shows another alternative embodiment of the present invention.
Figure 4:
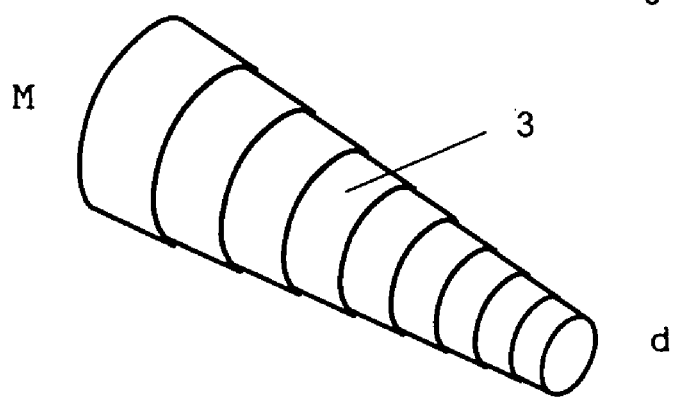
FIG. 4 shows a third alternative embodiment of the present invention.

As one alternative, the element has a frustroconical (1) shape, as shown in FIGS. 1 and 2; another alternative is a frustropyramidal (2) shape as seen in FIG. 3. Both alternatives permit the shaping of the element with a side profile that is not straight, or is stepped (3), as shown in FIG. 4. The element in FIG. 3 has a rectangular section (6).

Figure 5:
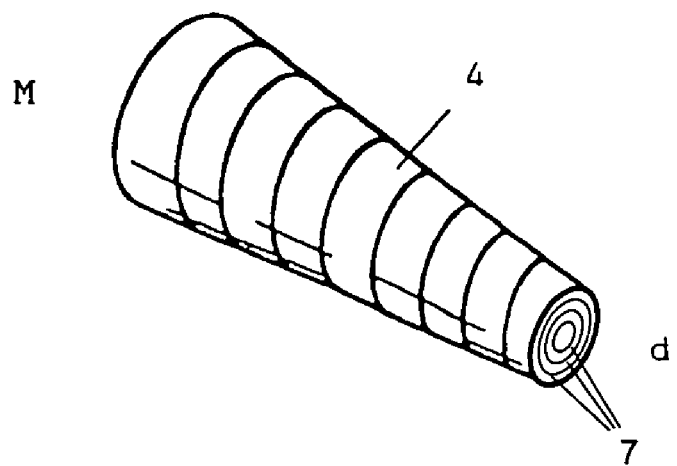
FIG. 5 shows a fourth alternative embodiment of the present invention.

Another alternative is by reshaping the outer surface of the frustroconical alternative into a helical shape (4) as shown in FIG. 5. The helical shaped element is constructed by wrapping a strip of cotton in successive concentric layers (7) with a higher number of layers on one end than the other.

The element is disposable and is preferably made of natural or artificial rubber, neoprene, cotton, or any other product of similar features.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method for aiding in the cementation of a fixed dental prosthesis, comprising:

providing a helically shaped block having a first end which is thicker than a second end, wherein the helical shape is formed by wrapping concentric layers of cotton;

positioning a dental prosthesis on the dental structure to which it is to be cemented;

placing the first end of said block mesially between two dental arcades and the second end of said block distally between the two dental arcades such that the dental prosthesis is positioned between the first and second ends of the block; and biting on the block to exert pressure at the first end equal to pressure exerted at the second end.

2. The method of claim 1, wherein the block is made of a material selected from the group consisting of natural rubber, artificial rubber, neoprene, and cotton.

3. A method for aiding in the cementation of a fixed dental prosthesis, comprising:

providing a frustroconically shaped block having a first end which is thicker than a second end, wherein the block is made of a material selected from the group consisting of natural rubber, artificial rubber, neoprene, and cotton;

positioning a dental prosthesis on the dental structure to which it is to be cemented;

placing the first end of said block mesially between two dental arcades and the second end of said block distally between the two dental arcades such that the dental prosthesis is positioned between the first and second ends of the block; and biting on the block to exert pressure at the first end equal to pressure exerted at the second end.

4. The method of claim 3, in which the block has a stepped profile.

* * * * *